United States Patent

Ries et al.

[11] 4,138,431
[45] Feb. 6, 1979

[54] REACTION OF α-PHOSPHORUS CONTAINING CARBOXYLIC ACIDS WITH PHOSPHOROUS ACID TO PREPARE SCALE AND CORROSION INHIBITORS

[75] Inventors: Donald G. Ries, Richmond; Joseph P. Maniscalco, Sugar Land, both of Tex.

[73] Assignee: Nalco Chemical Company, Oak Brook, Ill.

[21] Appl. No.: 920,615

[22] Filed: Jun. 29, 1978

[51] Int. Cl.² .................. C07F 9/38; C23F 11/00; C09D 5/08; C02B 5/06
[52] U.S. Cl. ..................... 260/502.4 P; 252/180; 422/15; 252/389 A
[58] Field of Search ................... 260/502.4 P

[56] References Cited

U.S. PATENT DOCUMENTS

| B 311,413 | 1/1975 | Velker et al. | 260/502.4 P |
| 2,957,931 | 10/1960 | Hamilton et al. | 260/502.4 P |
| 3,297,578 | 1/1967 | Crutchfield et al. | 260/502.4 P |
| 3,299,123 | 1/1967 | Fitch et al. | 260/502.4 P |
| 3,404,178 | 10/1968 | Roy | 260/502.4 P |
| 3,579,570 | 5/1971 | Nicholson et al. | 260/502.4 P |
| 3,734,954 | 5/1973 | Maier | 260/502.4 P |
| 3,933,944 | 1/1976 | Moreau et al. | 260/502.4 P |
| 4,077,997 | 3/1978 | Blum et al. | 260/502.4 P |

*Primary Examiner*—Joseph E. Evans
*Attorney, Agent, or Firm*—John B. Premo; Robert A. Miller; John S. Roberts

[57] ABSTRACT

Novel compounds and the use of these compounds in inhibiting corrosion and scale in open cooling systems containing ferrous materials which are:

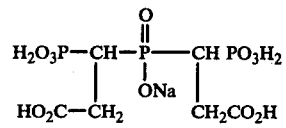

II

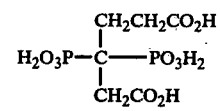

IV

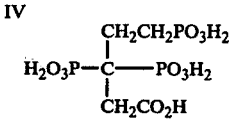

VI

These compounds are prepared by a carboxylic acid-phosphonic acid interchange in the general reaction involving α-phosphorous containing carboxylic acids as reactants:

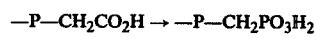

These compounds show activity in scale and corrosion inhibition in open air cooling systems.

4 Claims, No Drawings

REACTION OF α-PHOSPHORUS CONTAINING CARBOXYLIC ACIDS WITH PHOSPHOROUS ACID TO PREPARE SCALE AND CORROSION INHIBITORS

This invention relates to novel compounds and the use of these compounds in inhibiting corrosion and scale in open cooling systems containing ferrous materials. These compounds are:

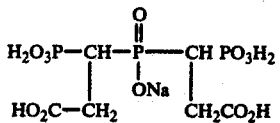

II

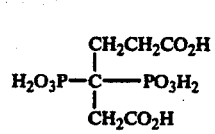

IV

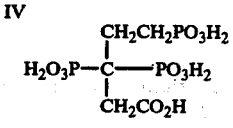

VI

The above compounds are prepared by a carboxylic acid-phosphonic acid interchange in the general reaction involving α-phosphorus containing carboxylic acids as reactants:

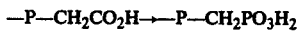

These compounds show activity in scale and corrosion inhibition in open air cooling systems. Included are alkali metal and ammonium salts of the products.

PRIOR ART STATEMENT

German Pat. No. 2,228,928 discloses a similar reaction for α-phosphorus containing carboxylic acids.

The present compounds and method relate to α-phosphorus containing acids certain members of which are useful as a scale inhibitor and show anti-corrosion activity especially in open cooling systems. The reaction, which may be viewed as a decarbonylation reaction, proceeds from α-phosphorus containing carboxylic acids which react with a trivalent phosphorus compound such as $PCl_3$ or $H_3PO_3$ to effect a carboxylic acid-phosphonic acid interchange. A reaction takes place between the carboxyl group which is α to a phosphorus atom in one reactant and the phosphorous acid reactant whereby the carboxyl group is replaced by a phosphonic acid group. In this process one mole of water and one mole of carbon monoxide are generated per carboxyl group being exchanged. A typical reaction starting with the 2:1 maleic acid-$NaH_2PO_2$ adduct is set out below:

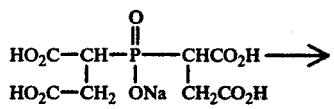

I

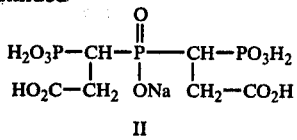

II

Compound II above gave 88% corrosion protection at 100 ppm compared with the starting material 2:1 adduct, which gave only 7% protection at 100 ppm.

An illustrative reaction noted from German Pat. No. 2,228,928 above is as follows:

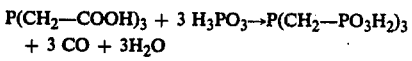

As reaction conditions it is noted that the reaction is carried out at a temperature of about 80–150° C and that in the reaction 1 mole of water is generated per carboxyl group. Suitable water binders in the reaction are as follows: acetic anhydride, phosphorus pentoxide or concentrated sulfuric acid. Inorganic drying agents, such as, for example, silica gel or anhydrous inorganic salts, which are capable of absorbing water of crystallization, such as sodium sulfate, magnesium sulfate, tertiary sodium phosphate, secondary sodium phosphate, can also be used.

The water binders are appropriately added in stoichiometric quantities and up to two to three times excess.

It is also possible to remove the water of the reaction without a water binder in such a manner that an inert gas is fed into the reaction mixture, for example, carbon dioxide, which will then carry the water of the reaction along. This mode of operation has proven to be expedient because, in this manner, the formation of foam, which occurs during the reaction due to the development of carbon monoxide gas, is reduced.

It is also possible to remove the water of reaction by azeotropic distillation with an inert solvent such as xylene.

In the use of phosphorous acid, it is noted that it is preferable to use 1 equivalent of phosphorus acid but 2 equivalents of phosphorus trichloride are indicated for utilization in the reaction.

The present reaction has been utilized to prepare novel compounds II, IV, and VI below from the adduct of maleic acid and sodium hypophosphite (I), Bayer PBS-AM (III) and Bayer AC2040 (V):

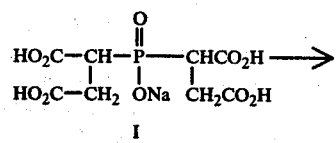

I

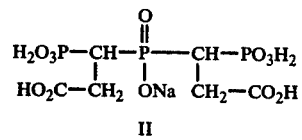

II

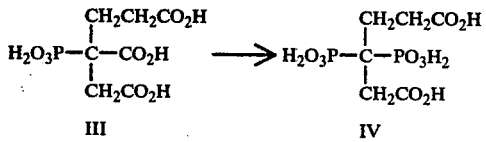

III          IV

-continued

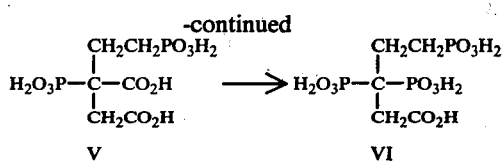

V → VI

These compounds, i.e., II, IV and VI are useful as corrosion and scale inhibitors together with the alkali metal and ammonium salts of the products.

TABLE 1

| Compound | Corrosion Inhibition % Protection | | | | | |
|---|---|---|---|---|---|---|
| | pH 6.5 | | | pH 8 | | |
| | 30 ppm | 100 ppm | 300 ppm | 30 ppm | 100 ppm | 300 ppm |
| I | — | — | — | — | — | —* |
| II | 63 | 93 | 93 | 75 | 83 | 85 |
| III | −33 | — | 35 | −54 | — | 43 |
| IV | 9 | — | 70 | 30 | — | 70 |
| V | 92 | — | 90 | 90 | — | 90 |
| VI | 90 | — | 92 | 49 | — | 71 |

*85% at 500 ppm.
Desired % protection is 50% at 30 ppm; 70-90% at 300 ppm.

TABLE 2

| Scale Inhibition | | |
|---|---|---|
| | "M" Limit | |
| Compound | 5 ppm | 10 ppm |
| I | 350 | 415 |
| II | 325 | 380 |
| III | 430 | — |
| IV | 450 | — |
| V | — | — |
| VI | — | — |

Reference = 3 ppm Dequest 2010 = 166 mv ≈ 400–450 M.
(Dequest 2010, 1-hydroxyethylidine-1,1-diphosphonic acid)

EXAMPLE 1

Product of Compound II

The exchange product (II) from the maleic acid-hypophosphite adduct was prepared as follows:

To a 2 l flask equipped with stirrer and condenser fitted with a Dean-Stark receiver was added 650g (1.0 mole) of a 50% aqueous solution of the maleic acid-hypophosphite adduct and about 300 ml of toluene. Most of the water was removed by azeotropic distillation. The toluene was decanted and 613 g (6 mole) acetic anhydride and 164 g (2 mole) phosphorous acid were added. The mixture was heated cautiously to about 80° when a vigorous reaction ensued accompanied by carbon monoxide evolution. When the reaction moderated, heating was continued at reflux for about 2 hours. After cooling, the acetic anhydride was decanted, water was added and the mixture heated briefly to insure complete hydrolysis of all reactants.

In other runs xylene was substituted for toluene and utilized in place of acetic anhydride to also remove water of reaction by azeotropic distillation.

We claim:

1. A compound selected from one member of the group consisting of

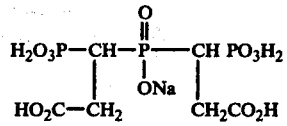

II

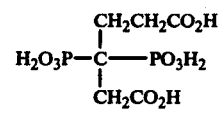

IV

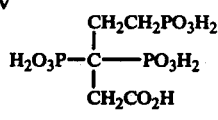

VI and alkali metal and ammonium salts thereof.

2.

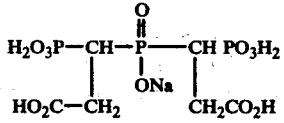

II according to claim 1.

3.

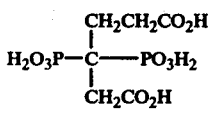

IV according to claim 1.

4.

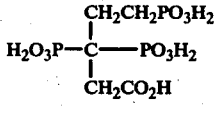

VI according to claim 1.

* * * * *